United States Patent [19]

Long

[11] Patent Number: 4,884,462
[45] Date of Patent: * Dec. 5, 1989

[54] CONVEYOR BELT CROSS-STREAM SAMPLING SYSTEM AND METHOD

[76] Inventor: John B. Long, 421 Heron Hill Dr., Louisville, Tenn. 37777

[*] Notice: The portion of the term of this patent subsequent to Sep. 2, 2003 has been disclaimed.

[21] Appl. No.: 285,322

[22] Filed: Dec. 13, 1988

Related U.S. Application Data

[63] Continuation of Ser. No. 915,746, Oct. 6, 1986, abandoned, which is a continuation-in-part of Ser. No. 688,394, Jan. 2, 1985, Pat. No. 4,619,149.

[51] Int. Cl.⁴ .............................................. G01N 1/12
[52] U.S. Cl. ................................................. 73/863.91
[58] Field of Search ................ 73/863, 863.01, 863.91, 73/863.92, 864.31, 864.32, 863.91

[56] References Cited

U.S. PATENT DOCUMENTS

| | | |
|---|---|---|
| 2,889,709 | 6/1959 | Blyth . |
| 3,181,369 | 5/1965 | Taylor . |
| 3,280,635 | 10/1966 | Cochet . |
| 3,487,427 | 12/1969 | Cahill . |
| 3,545,280 | 12/1970 | Sosney . |
| 3,791,218 | 2/1974 | Pennington . |
| 3,881,356 | 5/1975 | Palm . |
| 4,133,210 | 1/1979 | Jaeger . |
| 4,619,149 | 10/1986 | Long .................................. 73/863.91 |
| 4,682,664 | 7/1987 | Kemp ..................................... 73/1 B |

FOREIGN PATENT DOCUMENTS

| | | | |
|---|---|---|---|
| 1096656 | 1/1955 | Fed. Rep. of Germany . | |
| 2152804 | 10/1971 | Fed. Rep. of Germany . | |
| 2025908 | 12/1971 | Fed. Rep. of Germany . | |
| 2317588 | 10/1974 | Fed. Rep. of Germany . | |
| 0628424 | 8/1978 | U.S.S.R. ......................... | 73/864.32 |
| 0742752 | 6/1980 | U.S.S.R. ......................... | 73/863.91 |
| 0767609 | 9/1980 | U.S.S.R. ......................... | 73/863.91 |
| 0828005 | 5/1981 | U.S.S.R. ......................... | 73/863.91 |
| 0828007 | 5/1981 | U.S.S.R. ......................... | 73/863.91 |
| 1002886 | 3/1983 | U.S.S.R. . | |
| 1037121 | 8/1983 | U.S.S.R. . | |
| 1002135 | 8/1965 | United Kingdom . | |

OTHER PUBLICATIONS

Tema-Siebtechnik Advertisement, p. 17, CQ Fall 1983.
Tema-Siebtechnik Brochure "Automatic Mechanical Sampling Systems", Bulletin 8301; 1983; 6 pages.
Tema-Seibtechnik Sampling System Reference List; 5 pages, by Jul. 1985.;
"Tema-Siebtechnik Automatic Sampler Systems" publication by Jul. 1985; 17 pages.
Bristol Engineering Company Bulletin 101, entitled "Bristol DS Series Automatic DS Series Automatic Sampler for Conveyor-Handled Bulk Products"; 4 pages; 1977.
Bristol Engineering Company Bulletin 163, entitled "Bristol DS-3 Series Heavy Duty Belt Samplers"; 2 pages; Jul. 1985.
MSI Mini-Systems, Inc. brochure, entitled "Truck Sampling System" 4 pages; Oct. 1983.
Ramsey Engineering Co. brochure, 4 pages; by Jul. 1985.
HSS Co. brochure entitled "Sampling Systems"; 3 pages; by Jul. 1985.

*Primary Examiner*—Robert R. Raevis
*Attorney, Agent, or Firm*—Luedeka Hodges & Neely

[57] ABSTRACT

A method and apparatus are disclosed for cross-stream sampling of bulk material from a conveyor belt. The apparatus includes a sampler movable through an arcuate path across the conveyor belt for removing a cross-stream increment of bulk material from the belt. Provision is made for modulating the normal troughing of the conveyor belt and supporting and conforming the belt to the arcuate path of the sampler. When the conveyor belt is modulated to conform to the arcuate path of the sampler and the sampler moves through its arcuate path, the sampler moves in close proximity to the upper surface of the conveyor belt to remove the cross-stream increment of bulk material from the belt. The invention is capable of taking a cross-stream increment when the conveyor belt is stopped or moving. The ability to remove cross-stream increments from a moving belt eliminates interruptions in the flow of bulk material being conveyed on the belt.

14 Claims, 9 Drawing Sheets

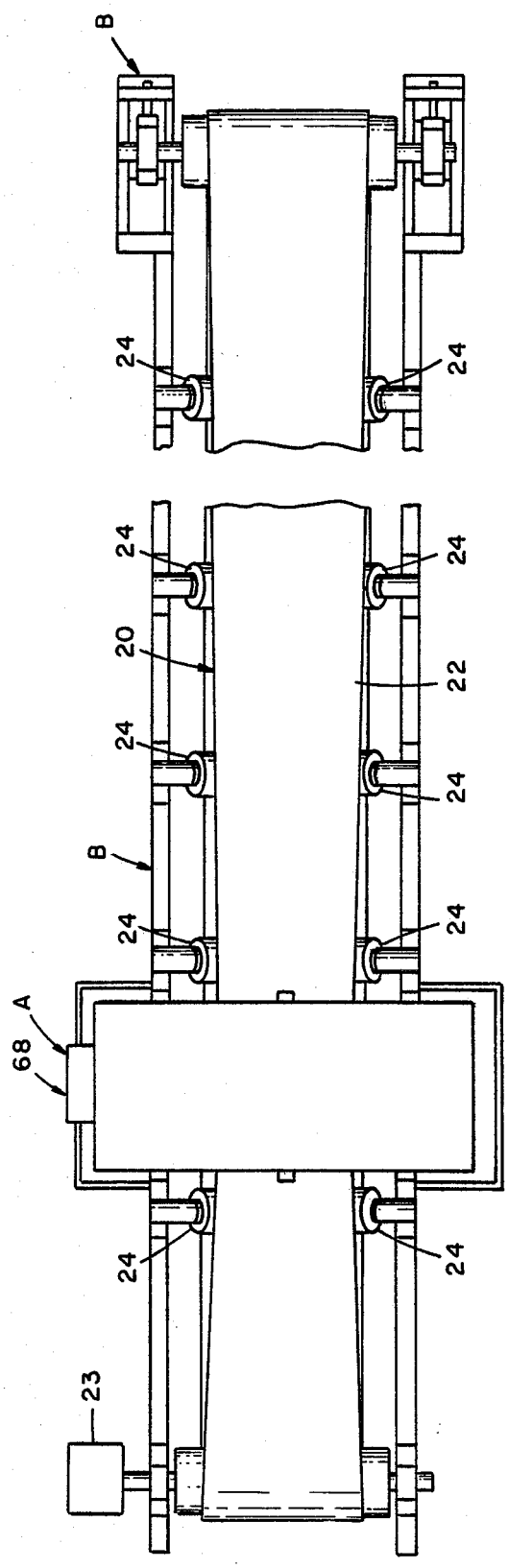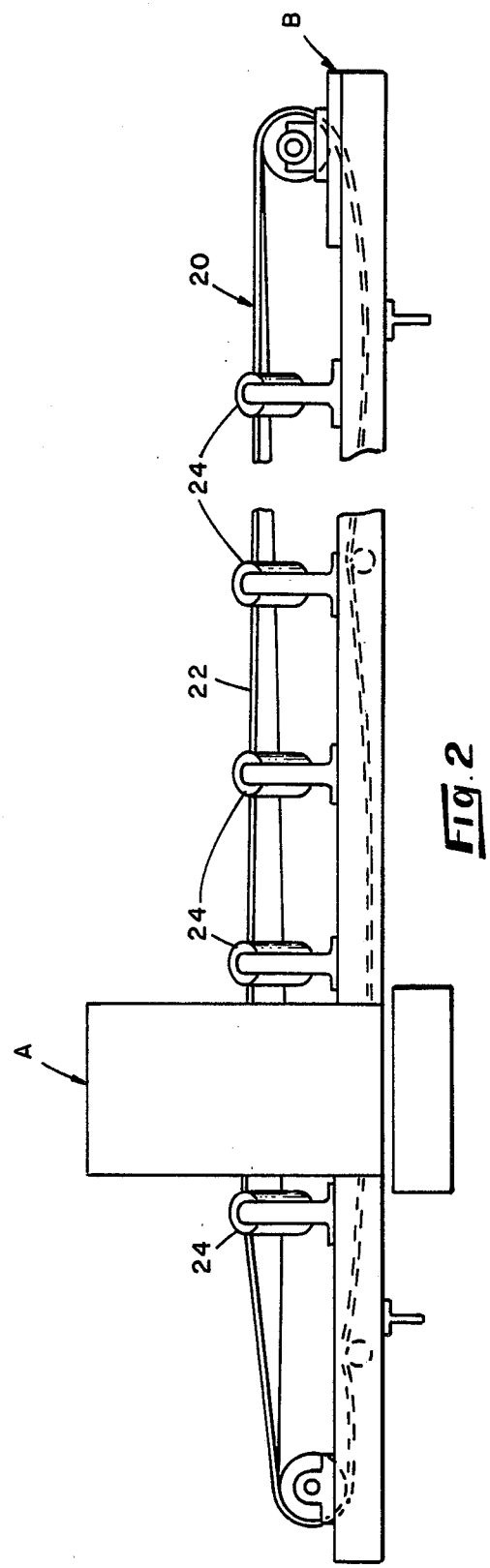

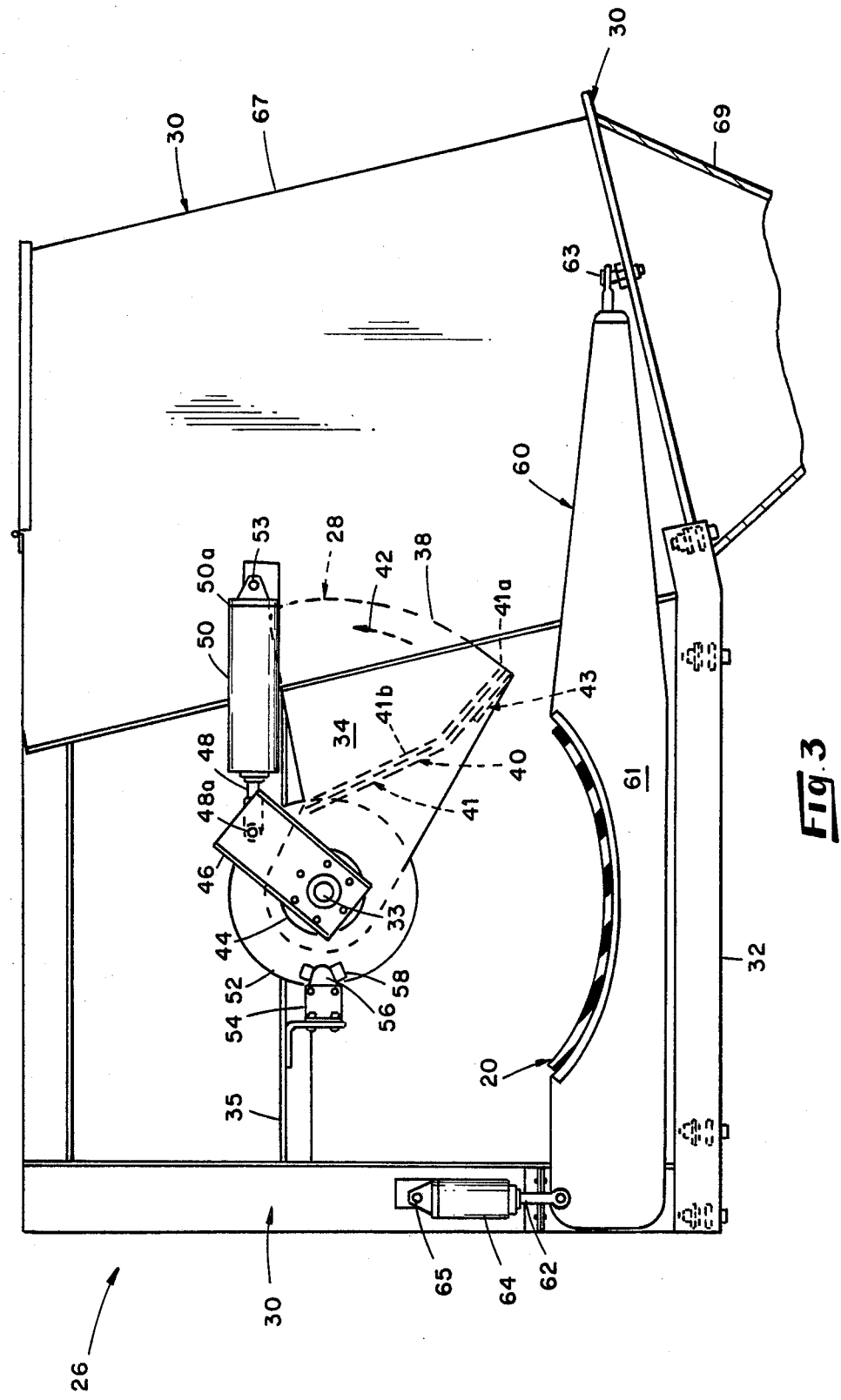

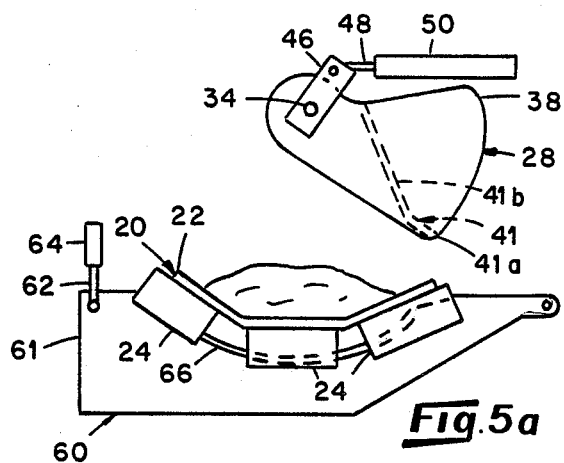
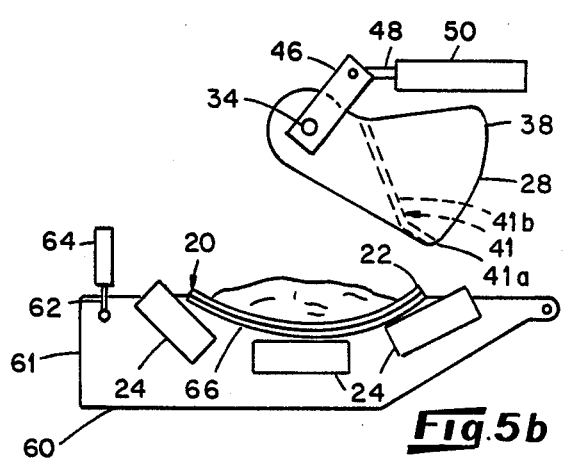
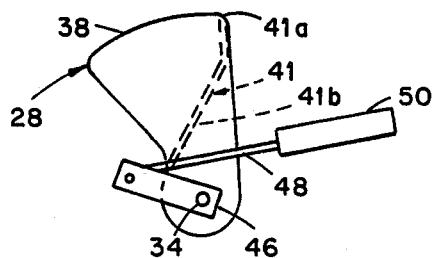
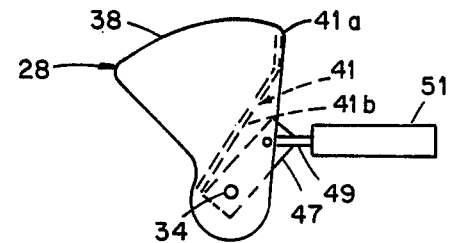
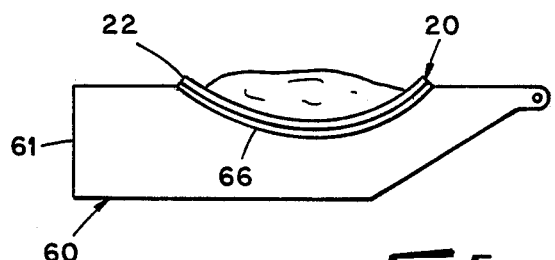
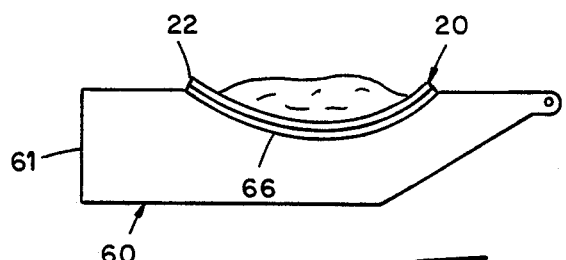
Fig.5c    Fig.5d
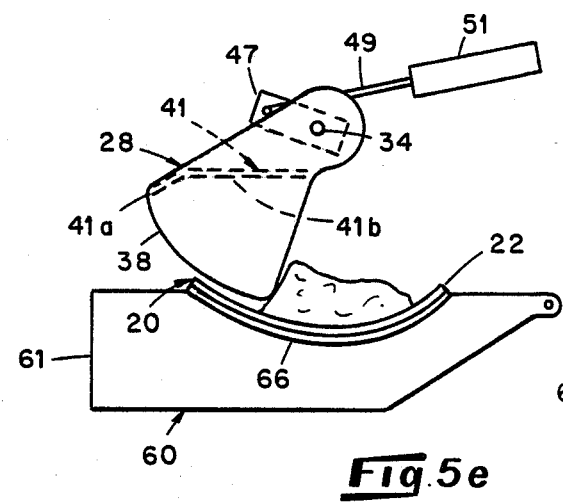
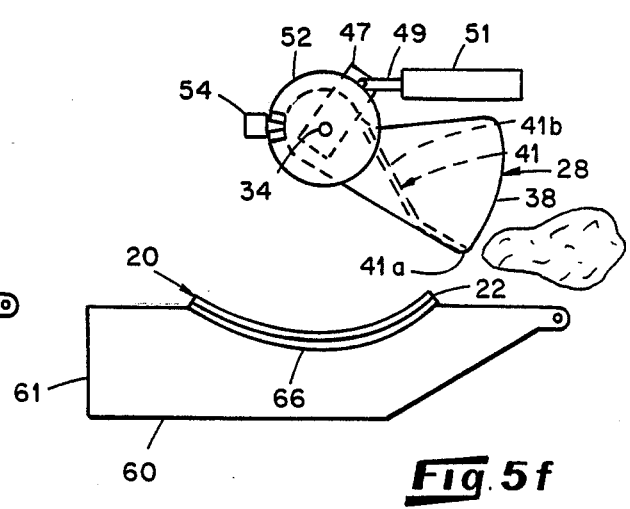
Fig.5e    Fig.5f

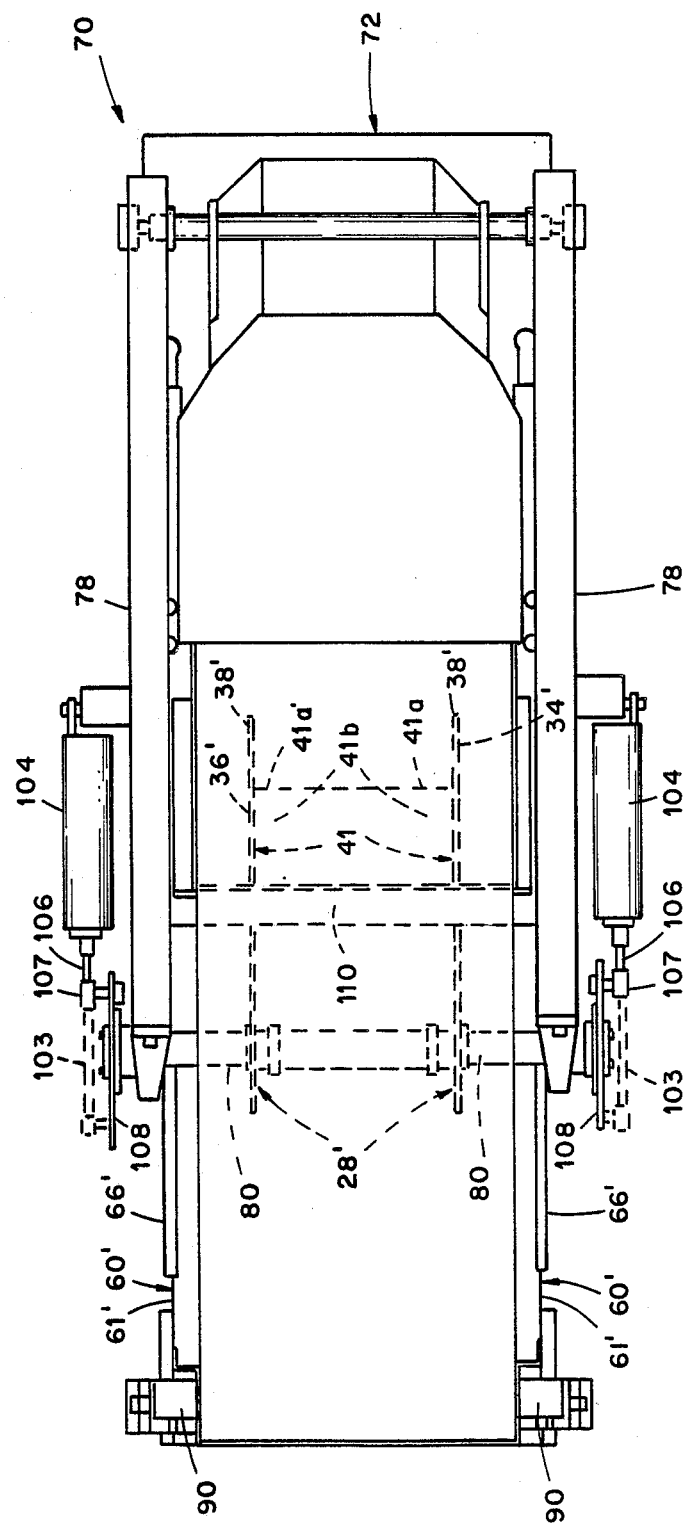

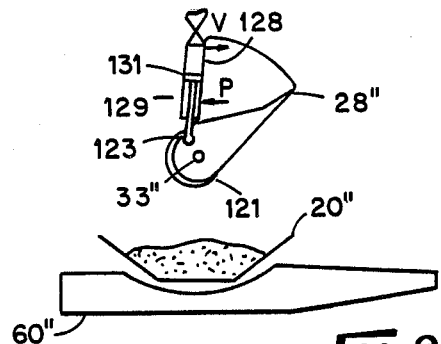
Fig.9a(1)
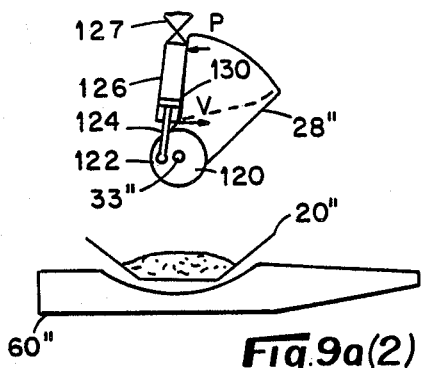
Fig.9a(2)
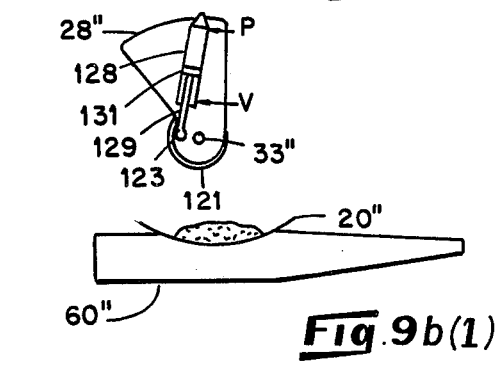
Fig.9b(1)
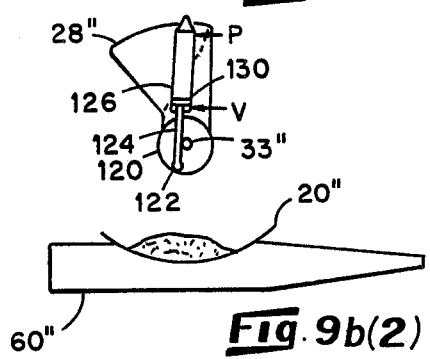
Fig.9b(2)
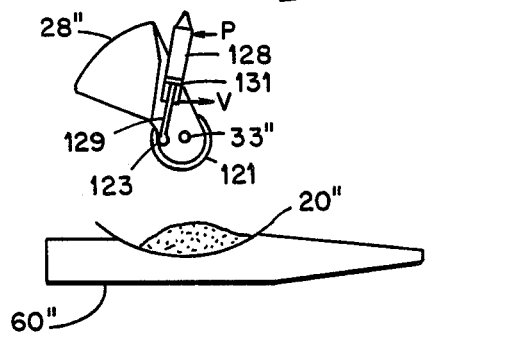
Fig.9c(1)
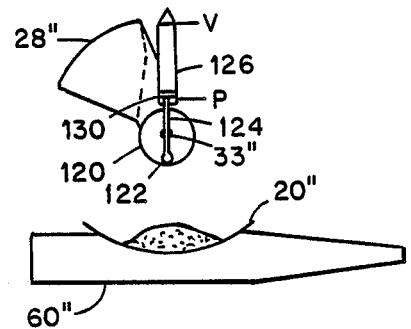
Fig.9c(2)

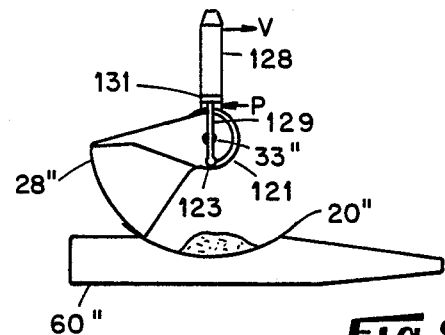
Fig.9d(1)
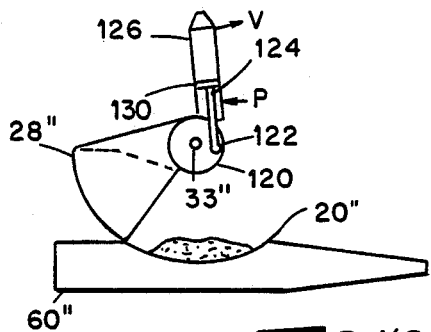
Fig.9d(2)
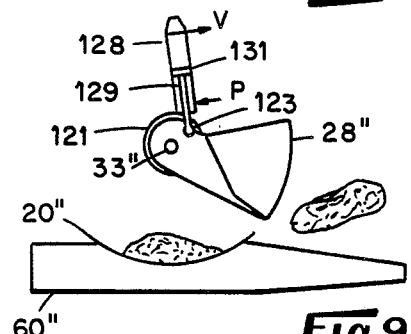
Fig.9e(1)
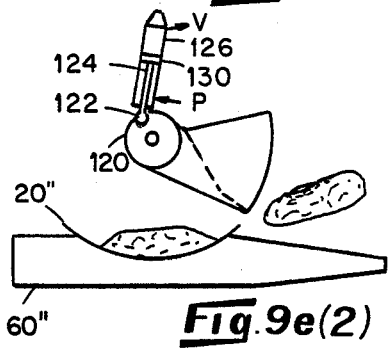
Fig.9e(2)
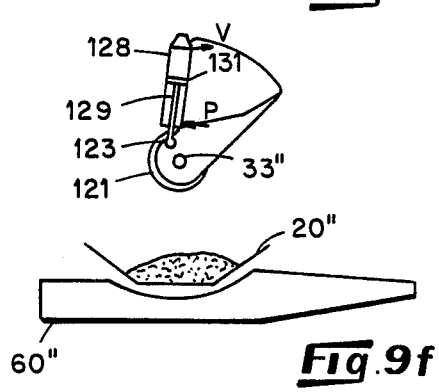
Fig.9f(1)
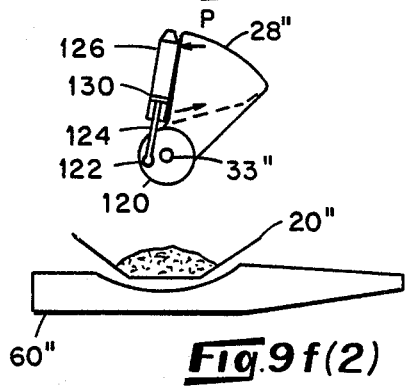
Fig.9f(2)
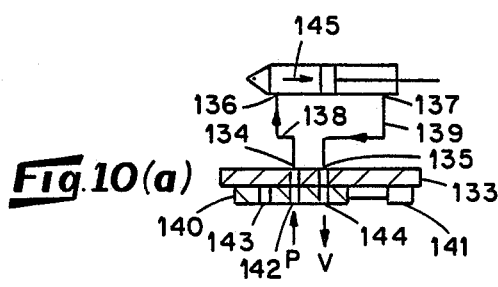
Fig.10(a)
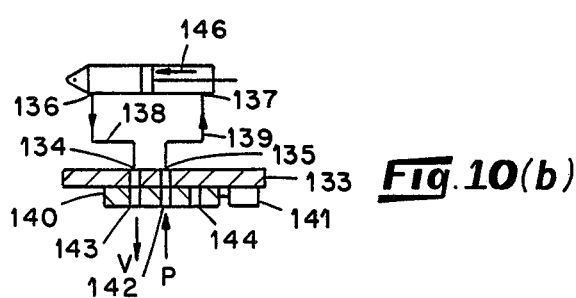
Fig.10(b)

CONVEYOR BELT CROSS-STREAM SAMPLING SYSTEM AND METHOD

This application is a continuation of application Ser. No. 915,746, filed Oct. 6, 1986 (now abandoned), which is a continuation-in-part of application Ser. No. 688,394, filed Jan. 2, 1985, now U.S. Pat. No. 4,619,149, issued Oct. 28, 1986.

This invention relates to improvements in the mechanized sampling of bulk material. In particular, the invention relates to cross-stream sampling of bulk material from a conveyor belt.

The invention was developed primarily for use in the incremental collection of samples of coal from a conveyor belt, and is therefore convenient to describe the same as used for such purposes. Of course, the invention can be used in the sampling of other bulk materials and is not to be construed as limited to the sampling of coal.

Belt conveyors are used in the majority of coal conveying facilities. Sampling from the conveyor belts presents a number of difficulties. For example, in the typical arrangement, the conveyor belt is supported on a plurality of spaced apart three roll idlers. The conveying surface of the belt thus presents faces that are angled with respect to one another making it difficult to remove a full cross-stream increment due to the angular recesses on the belt surface. Also, since the belts are flexible, they often sag between the idlers and also flex under sampling sweep arm pressures which adds to the difficulties involved in removing a complete sample. Similarly, since the belts of such belt conveyors have limited impact load capabilities, a sweep arm moving rapidly across the belt may impact against and drive coal lumps into the belt in a manner likely to stall, puncture, or damage the belt.

Accordingly, it is an object of this invention to provide a contour means for modulating the normal troughing of a conveyor belt and support and conform the same for facile removal of a cross-stream increment of a bulk material therefrom.

Belt conveyors subject to possible mechanical sampling installations include a full range of lengths from short feeder conveyors to overland conveyors spanning thousands of feet. Belt widths may vary from 14 to 96 inches. Belt speeds may vary from a slow creep for some feeders to as much as 1000 feet per minute. It is obvious that it would not be practical to intermittently stop a lengthy, high capacity belt conveyor for sampling purposes. Thus, it would be advantageous to obtain a cross-stream sample increment from a moving conveyor belt.

Mechanized sampling from a moving conveyor has been employed but the results have not been entirely satisfactory. For example, previous sweep samplers have tended to cross the moving belt relatively slowly. In the case of a fast moving belt, the relative speeds of the belt and the sampling mechanism moving across the belt cause the sample to be taken along a line which deviates excessively from a line perpendicular to the belt length. The result is excessive material disturbance and belt spill. Another problem has been that conventional sweeps do not adequately mate with the upper surface of the belt in their movement across the belt. This difficulty, combined with the sagging and puncture problems previously noted, further complicates the process of removing a cross-stream increment from a moving conveyor belt. Consequently, known sampling mechanisms have not been effective in removing acceptably representative cross-stream increment samples from a moving belt.

It is therefore another object of this invention to provide a mechanized sampling system for removing an acceptably representative cross-stream increment of bulk material from a moving conveyor belt.

These and other objects and advantages of the invention will become apparent upon consideration of the following detailed description when considered in conjunction with the accompanying drawings in which:

FIG. 1 is a somewhat diagrammatic top plan view of a conveyor belt for use in the cross-stream sampler of the present invention;

FIG. 2 is a somewhat diagrammatic side view of the conveyor belt of FIG. 1;

FIG. 3 is a side elevational view of one form of a sampling apparatus for use with the conveyor belt illustrated in FIGS. 1 and 2;

FIGS. 5a through 5f are diagrammatic views illustrating operation of the sampling apparatus shown in FIGS. 3 and 4;

FIG. 7 is a top plan view of the sampling apparatus of FIG. 6;

Figure 4:
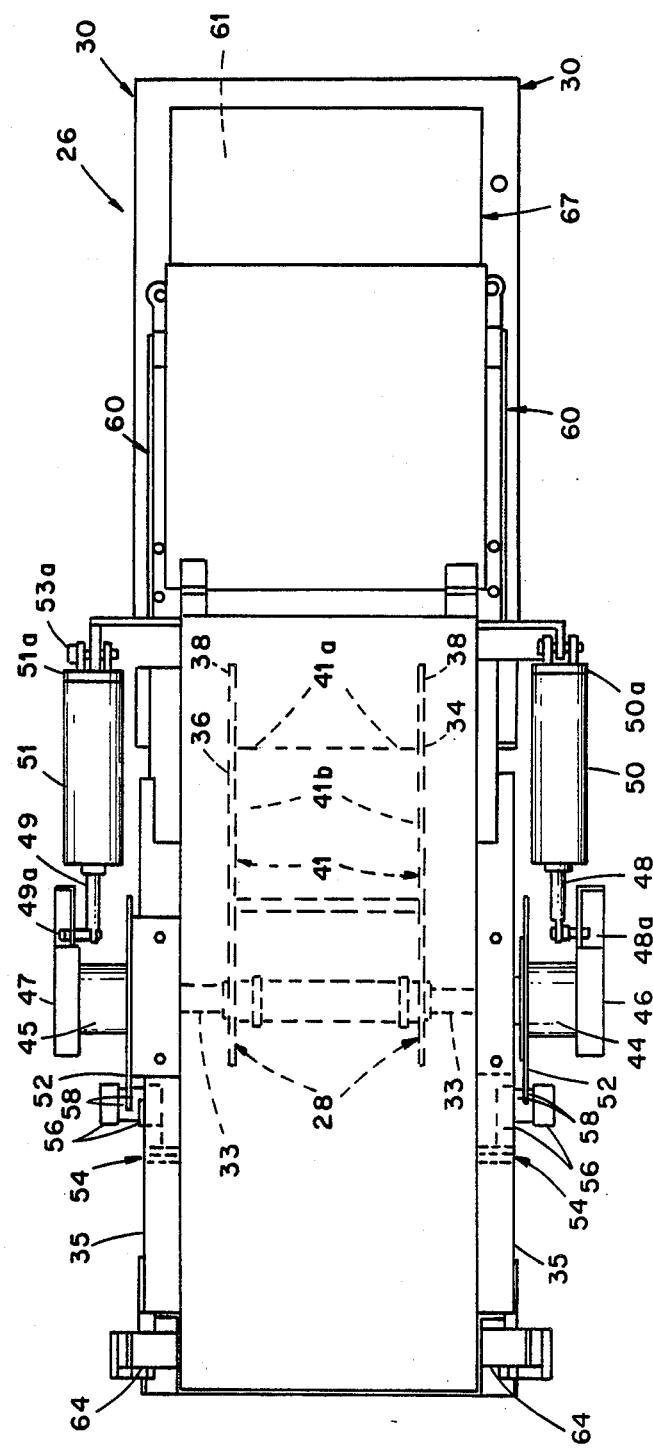
FIG. 4 is a top plan view of the sampling apparatus of FIG. 3.

FIGS. 9a through 9f are diagrammatic views illustrating operation of another embodiment of the invention; and FIGS. 10a and 10b are diagrammatic illustrations of a valve for use in the embodiment of FIGS. 9a through 9f.

Referring now to the drawings in which like reference characters refer to like or similar parts throughout the several views, FIGS. 1 and 2 illustrate the positioning of a sampling unit A adjacent a belt conveyor B. The views shown are intended to be illustrative generally of the incorporation of the sampling unit A into the belt conveyor B.

Generally, the sampling unit A is supported in an operative position over and adjacent to a continuous belt 20 for removing a cross-stream increment from a conveying reach 22 of the belt 20. A plurality of idlers 24 support the conveying reach 22 in a transverse trough-like configuration (see FIG. 5a) in a conventional manner so that the reach 22, viewed in cross-section, has angled sides relative to a center position thereof. The belt 20 is driven by any suitable means as, for example, by a drive motor 23 located adjacent one of its ends. As illustrated, the sampling unit A is positionable to be located astraddle the conveying reach 22 of the belt conveyor B at any desired location along its length.

One form of the sampling unit A is illustrated in FIGS. 3 through 5 and includes a sampling apparatus 26 comprising a sampler 28 rotatably mounted on a frame structure 30 fabricated from suitable structural members. Sampler 28 is rotatable in a plane substantially perpendicular to the direction of movement of the conveying reach 22 and thus moves transversely of the belt 20. Frame structure 30 includes a base 32 which may be secured to the supporting structure of the belt conveyor B beneath the conveying reach 22. Sampler 28 is preferably fixedly mounted on a shaft 33 which is rotatably mounted on transversely extending support members 35 extending across opposite sides of the frame structure 30 and spaced apart longitudinally of the direction of movement of the belt 20. Thus, the shaft 33 is supported over and above the conveying reach 22 and aligned parallel to the line of movement of the belt 20.

Sampler 28 includes side or divider plates 34 and 36 each having one end rigidly attached to shaft 33 for rotation therewith. The plates 34 and 36 are spaced-apart preferably a distance of not less than three times the diameter of the largest piece of bulk material being conveyed on the conveying reach 22. The end of each of the plates 34 and 36 is provided with an arcuate edge 38, all portions of which are substantially the same radial distance from the shaft 33. The radially outermost point on the edges 38 defines the extremity of the path of arcuate movement of sampler 28.

In order to sweep material from the belt, a back plate or sweep 41 is provided between the plates 34 and 36. The sweep 41 is fixedly connected between the side plates 34 and 36 and includes a radially outermost edge 41a positioned adjacent the arcuate edges 38 of the side plates 34 and 36 so that the sweep 41 extends radially outwardly of the shaft 33 and terminates in close proximity to the arcuate edges 38 of the side plates 34 and 36.

The sweep 41 and the side plates 34 and 36 are preferably arranged so that sampler 28, when viewed in cross-section, is in the shape of an open-ended rectangle. The arrangement provides that the side plates 34 and 36 divide and segregate the cross-stream increment ahead of the sweep 41 as the sampler 28 is rotated across the conveying reach 22. Also, the length of the portion of the arcuate edges 38 between which a sample is segregated is preferably determined to provide a circumferential dimension of the sampler 28, as viewed in FIG. 3, which encompasses at least a substantial portion of the reach 22 when the sampler 28 is moved across the reach 22. This aids in minimizing the "wave effect" which can arise if the capacity of the sampler 28 is exceeded before its leading edge has reached the opposite side of the reach 22, causing a large portion of the remaining material in the cross-section increment to be pushed out to the side of the path of the approaching sampler 28 in waves and thus escape removal. Providing the described dimensional relationship between the arcuate edges 38 and the reach 22 therefore aids in ensuring that the sample obtained is a substantially complete cross-stream increment of the material on the reach 22.

The sampler 28 is rotated in the direction of the arrow 42 in FIG. 3 and, in order to eject material from the conveying reach 22, the sweep 41 is preferably configured so that the position of its leading surface 41b is advanced in the direction of rotation of the sampler 28 at progressively radially inward locations on the surface 41b from the outer edge 41a. Consequently, when sampler 28 is rotated, the sweep 41 will impart a force to an increment on the belt which will cause it to be ejected from the sampler 28 as will be hereinafter described.

Preferably, wiper means 43 is mounted to the rearward side of the back plate 41 so as to trail the back plate 41 and substantially remove any bulk material remaining on the reach 22 as sampler 28 is rotated through the bulk material. Wiper means 43 may be fabricated from a deformable material such as rubber or plastic, or may be in the form of flexible bristles.

In order to effect rotation of the shaft 33 and the sampler 28, the opposite ends of the shaft 33 are each connected to one side of an overriding clutch 44 or 45. The other side of the overriding clutches 44 and 45 are connected to torque arms 46 and 47, respectively. Each of the torque arms 46 and 47 is adapted to be rotated by pneumatic cylinders 50 and 51, respectively. To this end the base ends, 50a and 51a, are connected to the frame 30 by suitable connectors such as pivot pins 53 and 53a. Piston rods 48 and 49 of the respective pneumatic cylinders 50 and 51 are pivotally connected to their related torque arm 46 or 47 as by the pivot pins 48a and 49a.

In order to rotate the sampler to obtain a high sampling speed, high pressure air is admitted to the cylinders 50 and 51 sequentially to attain maximum acceleration and peripheral speed as will be described hereinafter. The provision of the overriding clutches 44 and 45 permits either of the cylinders 50 or 51 to effect rotation of the shaft 33 because driving of the shaft 33 is only effected as the piston rods 48 and 49 are moving out of their respective cylinders 50 and 51.

Braking of the sampler 28 is accomplished through disc brakes. Brake disks 52 are rigidly attached to shaft 33 at each of its ends for rotation therewith. They are spaced inwardly of the clutches 44 and 45 and located adjacent the support members 35. Braking means 54 is mounted on each of the support members 35 and includes pneumatically actuated calipers 56 for clamping opposed shoes 58 against the surfaces of the disk 52 to stop rotation of the sampler 28 and to hold the sampler 28 in a desired disposition relative to the conveying reach 22.

Below sampler 28 and extending transversally of and beneath the conveying reach 22 are a pair of longitudinally spaced-apart contour plate assemblies 60. The contour plate assemblies 60 are each preferably positioned between a pair of adjacent idler roller sets 24 and, when in their retracted positions (see FIG. 5a), are below the normal path of the conveying reach 22. Each of the assemblies 60 includes an elongate beam 61, one end of which is pivotally mounted as at 63 on the frame 30. The beams 61 are connected at their other ends to piston rods 62 of pneumatic cylinders 64 which are attached to the frame 30 by pivot pins 65. The cylinders 64 are operable to raise and lower the beams 61. Arcuate belt supporting plates 66 are provided on the upper surfaces of the beams 61 which are configured with a radius corresponding substantially to the radius of the arc circumscribed by the radial extremity of the arcuate edges 38 of sampler 28.

As diagrammatically shown in FIGS. 5a through 5e, the assemblies 60 are normally located below the conveying reach 22 and, on actuation of the cylinders 64, are pivoted upwardly against the conveying reach 22 to lift and contour the conveying reach 22 so that it has a transverse arcuate configuration which substantially conforms to the radius of the arc as circumscribed by the radial extremity of the arcuate edge 38 of sampler 28 as it moves across the reach 22. This position of the assemblies 60 is illustrated in FIG. 3 and in FIGS. 5b through 5e. Thus, the assemblies 60 modulate the normal troughing of the conveying reach 22 in a manner to facilitate a clean sweep of sampler 28 across the belt and also serve to support the belt 20 in the area swept by the sampler 28 so as to substantially eliminate the possibility of puncture of the belt 20 by any sharp edged particles as they are being removed from the reach 22.

The right-hand side of the frame 30 as viewed in FIG. 3 supports a housing 67 for directing the material comprising the cross-stream increment removed from the belt 20 into a chute 69 through which it is discharged for further treatment.

Control means 68 (see FIG. 1) may be mounted on the frame 30 of the sampling apparatus 26 for systematic operation of the sampling unit A, i.e. for sequentially actuating the contour plate assemblies 60 to raise and conform a portion of the conveying reach 22 of the belt 20 to an arcuate configuration which substantially conforms to the radial path of sampler 28; selectively actuating the cylinders 50 and 51 to impart a rotational force on the sampler 28 causing the latter to rotate on the shaft 33 to segregate and remove a cross-stream increment of bulk material from the contoured conveying reach 22; actuating braking means 54 to stop the rotation of sampler 28 after removal of the cross-stream increment; and lowering the contour plate assemblies 60 to resume normal troughing of the conveying reach 22 of the belt 20 on the idlers 24.

Control means 68 is preferably preset in accordance with predetermined timing or location as to sample taking, free of selection on a discretionary basis by an operator, and is operative such that the systematic and sequential operation thereof is performed within a very short period of time. As will be described, the sampling apparatus 26 is capable of effectively removing a cross-stream increment of the bulk material while the belt 20 is moving and thus eliminates the need for surge capacity on the conveyor B upstream of the sampling location.

As previously indicated, the operation of the sampling apparatus 26 is illustrated diagrammatically in FIGS. 5a through 5e. Normal troughing of the conveying reach 22 prior to sample removal is shown in FIG. 5a. The conveying reach 22 rests on the idler rolls 24 in its normal, angled configuration and is carrying the material to be sampled. Preferably, at a prescribed interval and while the belt 20 is moving at its normal speed, a cross-stream increment sample is taken. The first step is to activate the cylinders 64 to raise the contour plate assemblies 60 which disposes the surfaces of the arcuate contour plates 66 against the lower surface of the conveying reach 22, lifting the same off of the idlers 24 and supporting the reach 22 in conformity with the configuration of the contour plates 66 as shown in FIG. 5b. The positions of the cylinders 64 and length of their strokes are determined so as to present the upper surface of the conveying reach 22 in an arcuate configuration substantially that of the arc circumscribed by the extremity of the arcuate edges 38 of sampler 28.

After the conveying reach 22 has been modulated as shown in FIG. 5b, cylinder 50 is connected to a source of high pressure air to external piston rod 48 out of the cylinder 50 to impart a force on torque arm 46. The overriding clutch 44 is thereby engaged to transmit the force applied to the torque arm 46 to rotate shaft 33 and its associated sampler 28. This initiates a counterclockwise rotation of sampler 28 as viewed in FIG. 5. As the rod 48 is extended out of the cylinder 50, sampler 28 accelerates through an arc of approximately 120° to the end of the stroke of the cylinder 50. This position is illustrated in FIG. 5c.

Preferably, at about the time cylinder 50 reaches the end of its stroke, high pressure air is delivered to the cylinder 51 located at the other end of the shaft 33 (see FIG. 5d). This extends the rod 49 out of cylinder 51 imparting a force against torque arm 47 which is transmitted through the overriding clutch 45 and shaft 33 to sampler 28, imparting additional momentum to sampler 28. Continued extension of the rod 49 out of the cylinder 51 and the forces of gravity further accelerate sampler 28 through a next approximately 120° arc to a position approximated by the configuration shown in FIG. 5e. At this point, sampler 28 has been accelerated to a very high velocity moving across the modulated reach 22 at a speed of over about 180 inches per second. The side plates or dividers 34 and 36 segregate the cross-stream increment and the back plate or sweep 41 throws the increment from the conveying reach 22 as shown in FIG. 5f.

Impact of sampler 28 against the bulk material slows it slightly and when it reaches the position approximated by the configuration illustrated in FIG. 5f, brake means 54 is activated to stop the sampler 28 in its ready position. The cylinders 64 are then deactivated to lower the contour plate assemblies 60 and normal conveying is resumed as shown in FIG. 5a. Sampler 28 may be held in its ready position by brake means 54 which are then released upon initiation of the next sampling sequence.

Tests have shown that reliable cross-stream sampling can be effective even on belts operating at high speeds. This is believed to be due to the interaction of the belt modulation and the higher sampler speeds employed.

Figure 6:
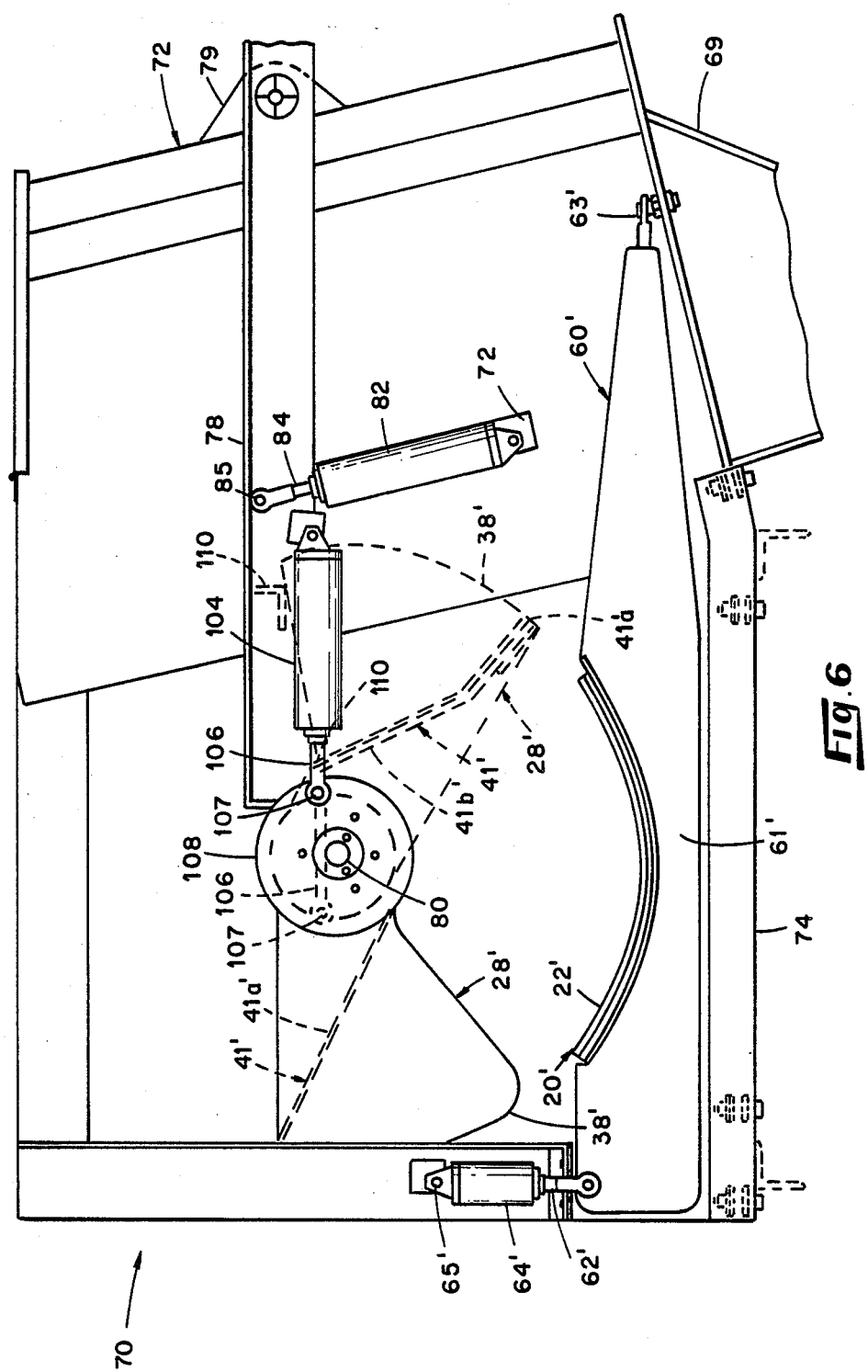
FIG. 6 is a side elevational view of another embodiment of the sampling apparatus.

An alternate embodiment of the sampling unit is illustrated in FIGS. 6 and 7. Sampling apparatus 70 includes a frame 72 on which is supported a contour plate assembly 60' which is substantially identical, in construction and operation, to the contour plate assembly 60 which has been described. Accordingly, the corresponding parts are given corresponding numbers suffixed with the prime symbol and reference is made to the previous description of those parts and their operation. It also includes a sampler 28' which is substantially similar to sampler 28 and includes side plates or dividers 34' and 36' and a back plate 40', etc., all of which correspond to the same parts with similar reference numerals as employed in connection with sampler 28.

Sampler 28' is fixedly attached to a shaft 80 for rotation therewith. Shaft 80 is journalled in bearings on a pair of spaced apart lift arms 78 which are pivotally mounted for vertical movement in gussets 79 on the frame 72. Intermediate their ends, each of the lift arms 78 are supported by pneumatic cylinders 82 mounted on the frame 72 and whose pistons 84 are attached to pins 85 on arms 78. Actuation of the cylinders 82 causes the sampler 28' to be raised from a position in which its radial path corresponds to the arc of the modulated reach 22' to a position where the radial path is above any material on the reach 22'.

A preferred means for inducing rotation of sampler 28' includes the use of pneumatic cylinders 104 and their associated piston rods 106. Each cylinder 104, as illustrated, is connected to one of the lift arms 78, and the associated piston rods 106 are pivotally connected by pins 107 to crank arms in the form of disks 108 fixedly attached to opposite ends of the shaft 80. The rods 106 are connected to the disks 108 on their outer sides to provide rotation of the discs 108 incident to movement of the piston rods 106.

When sampler 28' is in the ready position, as shown in full outline in FIG. 6, the rods 106 are fully retracted in the cylinders 104. Activating the cylinders 104 extends the rods 106 which imparts a force on the disks 108, inducing movement of sampler 28' downwardly through an arc across the conveying reach 22 to the position shown in dotted outline in FIG. 6. At this point, sampler 28' has been rotated through approximately 145° and the rods 106 are fully extended out of the cylinders 104. It should be noted that the piston rods 106 do not pass over center so that retraction of the pistons 106 will cause the sampler 28' to return to its starting position.

A shock absorbing bar 110 may be provided spanning between the lift arms 78 and positioned to engage sampler 28' and prevent its rotation substantially beyond the finished position.

Figure 8A:
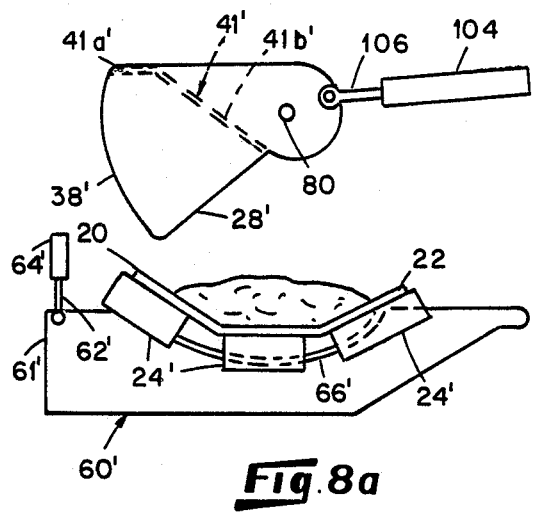
FIGS. 8a through 8d are diagrammatic views illustrating operation of the sampling apparatus shown in FIGS. 6 and 7.
Figure 8B:
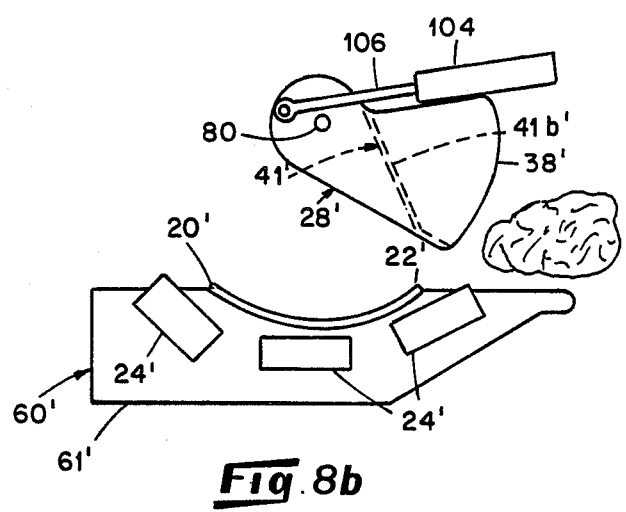

The steps of sampling are illustrated diagrammatically in FIGS. 8a through 8d. Specifically, FIG. 8a represents sampler 28' in the ready position and the conveying reach 22' normally troughed in the idlers 24'. As the first step, the cylinder 64' is actuated to lift beam 61' to modulate the shape of the reach 22' into an arc whereupon high pressure air is supplied to cylinders 104 extending rods 106 to cause the sampler 28' to traverse the reach 22' and to eject the cross-stream increment as shown in FIG. 8.

Figure 8D:
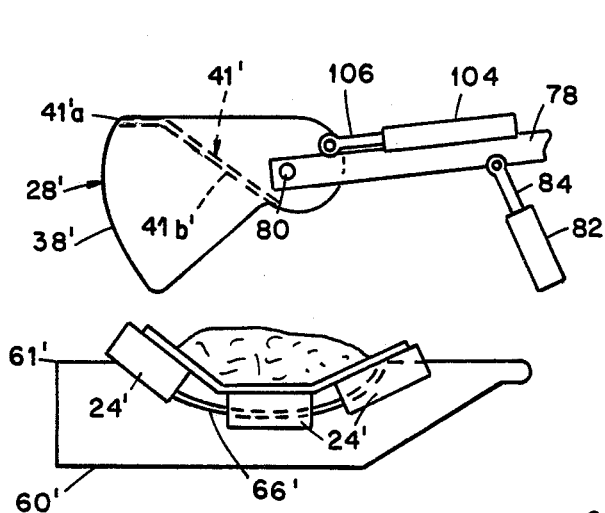
Figure 8C:
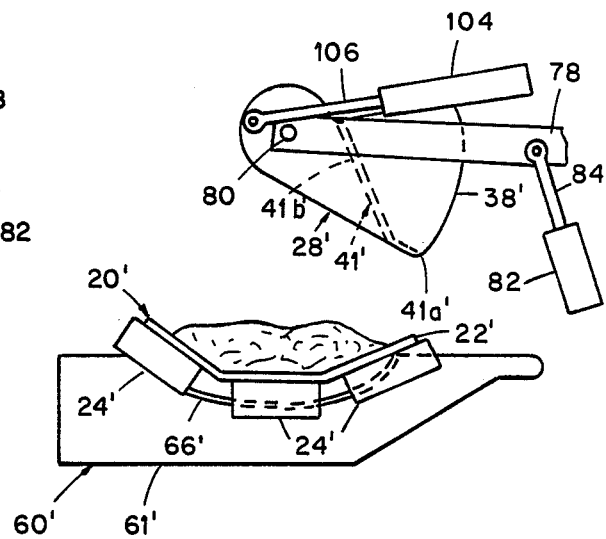

Following ejection of the sample, the cylinder 64' is activated to drop the reach 22' back onto the idler rolls 24'. The cylinders 82 are activated to raise lift arms 78 to a position above the reach 22' so that rotation of sampler 28' back to the other side of the reach 22' can be accomplished without the sampler 28' interfering with the flow of material on belt 20'. The positions of the equipment are then as shown in FIG. 8c. The rods 106 of cylinders 104 are then retracted and the cylinders 82 are operated to retract rods 84, lowering sampler 28' to its ready position as shown in FIGS. 8a and 8d.

Another embodiment of the invention is illustrated diagrammatically in FIGS. 9a-f and 10a-b. This embodiment is operable to position the divider sweep at a predetermined rest position without the use of brakes or stops and to accelerate and power the sweep in a highly efficient manner across the modulated belt.

The embodiment includes a sampler 28" which is substantially similar to samplers 28 and 28' described above and is mounted on a shaft 33" for rotation therewith. Crank discs 120 and 121 are rigidly attached to the opposite ends of the shaft 33". The crank discs 120 and 121 are provided with crank pins 122 and 123, respectively. The crank pins 122 and 123 are angularly offset from one another, preferably from about 40 to about 90 degrees, and most preferably from about 60 to about 75 degrees.

Crank pin 122 is operably connected to the rod 124 of a pneumatic cylinder 126, the base of which is supported on a frame 127 (shown only in FIG. 9(a) and omitted thereafter for clarity). A second pneumatic cylinder 128 has its base connected to the frame 127 and its rod 129 connected to crank pin 123. Of course, the rods 124 and 129 are connected to pistons 130 and 131, respectively, in the usual manner.

Each of the cylinders 126 and 128 is provided with air ports at their opposite ends so that they are operable in a double acting mode. The ports of each of the cylinders are preferably connected to a control valve which will pressurize one end of the associated cylinder and vent the other. Various commercial valves are readily available for this purpose. Basically, all of the valves operate with a slide or rotary member, operated by an actuator such as a solenoid to control the airflow as desired.

One such valve is diagrammatically shown in FIGS. 10a and b. The valve includes a base plate 133 having two ports 134 and 135 which are connected to ports 136 and 137 on the cylinder to be actuated via conduits 138 and 139.

Adjacent the base plate 133 is a slide 140 which is movable in sealing relationship with the base plate from the position shown in FIG. 10a to the position shown in FIG. 10b by means of a solenoid 141. The slide 140 is provided with a central port 142 which is connected to a source of pressurized air and which is movable under the action of the solenoid 141 to communicate with either the port 134 or the port 135. Vent ports 143 and 144 are provided in the slide on each side of the pressure port 142 to communicate with whichever of the ports 134 and 135 is not pressurized by port 142 in the slide 140.

In operation, when the slide is in the position shown in FIG. 10a, pressurized air is admitted to the cylinder through the conduit 138 and the port 136. Simultaneously, port 137 is vented through line 139 and ports 135 and 144. This causes the piston to move in the direction of arrow 145. Actuation of solenoid 141 moves the slide to the position shown in FIG. 10(b) whereupon port 137 is pressurized and port 136 is vented, thus causing the piston to move in the direction of arrow 146.

Now, again referring to FIGS. 9a-f, each of the Figures is directed to the position of the sampler 28" and the cylinders 126 and 128. During various stages of the sampling operation, the Figures followed by the numbers (1) and (2) are directed to the upstream and downstream cylinders at the same time, (1) referring to the position of the downstream cylinder 128 and (2) referring to the position of the upstream cylinder 126. On the drawings the ports for the cylinders which are supplied by the cylinder valves are shown diagrammatically by the heavy arrows which are marked with the letters "P" and "V" representing admittance of pressurized air and venting, respectively.

FIGS. 9a(1) and (2) show the two cylinders 126 and 128 and sampler 28" in the rest position. In that position, the crank pins 122 and 123 are preferably angularly spaced apart, approximately 90°, and cylinder 126 has its base port pressurized and its rod end port vented with the piston 130 of the cylinder 126 being ahead of dead center. The cylinder 128 has its rod end port pressurized and its base end vented with the piston 131 being approximately midway between the ends of the cylinder 128. In this position, the forces exerted by the cylinders 126 and 128 are balanced and the sampler 28" is stationary above the belt 20".

Referring now to FIGS. 9b(1) and (2), the contour plate assembly 60" is raised to contour the belt 20" into an arcuate path and the valve controlling the downstream cylinder 128 is actuated to pressurize the base end of cylinder 128 and to vent the rod end. At this point, the sampler 28" is rotated by the dual action of the two cylinders 126 and 128 working together to cause rapid acceleration.

At about the time the crank pin 122 of cylinder 126 reaches dead center, the valve controlling cylinder 126 is actuated to pressurize the rod end of cylinder 126 and to vent the base end. The positions of both cylinders 126 and 128 are shown in FIGS. 9c(1) and 9c(2). This causes the sampler 28" to again be accelerated by the two cylinders simultaneously.

At the time the rod 129 from cylinder 128 reaches approximately dead center, the valve controlling that cylinder is actuated to cause pressurize air to be applied to the port at the rod end of the cylinder 128 and to vent the port at the base end. This condition is shown in FIGS. 9d(1) and (2). Again, as the sampler 28" is passing across the belt 20", it is being powered by both cylinders.

As the sampler 28" leaves the belt 20 and ejects the sample as shown in FIGS. 9e(1) and (2), the cylinder 126 has passed dead center so that the cylinder 126 opposes the action of the cylinder 128. This causes the sampler 28" to eject the sample increment at a predetermined trajectory. The valve controlling the air supply to the cylinder 126 is preferably timed to provide about a 100 millisecond delay past dead center position of cylinder 126 after which it is actuated to pressurize the base end of cylinder 126 and to vent its rod end. This causes the sampler 28" to come to rest in its original position because of the bucking action of the cylinders 126 and 128 (see FIGS. 9f(1) and (2)). This completes the cycle. Of course, the contour plate assembly 60" is dropped so that the belt 20" returns to its unmodulated condition.

As is apparent, the described construction results in substantial forces on the sampler 28" to effect rapid acceleration and slows and positions the sampler 28" without need for stops, brakes or clutches.

It should be appreciated that numerous advantages are provided by the invention arising, for example, from the structure associated with producing sample taking speeds sufficiently high so as to enable removal of an acceptably representative cross-stream sample of the bulk material from a moving conveyor. By way of example, several advantages of the present invention may be illustrated in the context of a belt conveyor moving at a rate of about 550 feet per minute conveying approximately 1200 tons of coal per hour with the largest expected lump size being about 2 inches in diameter. The conveyor belt has a width of 42 inches and carries a 36 inch wide stream of coal.

The width between the side plates of the sampler is about six inches since, for adequate sampling, it should be at least three times the largest size encountered.

In each of the described embodiments the sampler can be accelerated to a velocity of 180 inches per second or more by the time it impacts the bulk material on the belt. The resulting traversal of the modulated belt is achieved in a small fraction of a second to remove the sample increment. The sample obtained is an acceptably representative sample according to ASTM Type I condition B criteria for coal applications.

The preferred forms of the invention also employ the additional feature of means for modulating the normal troughing of the belt to support and conform the belt to the arcuate path of the extremities of the sampler so that the arcuate divider edges of the sampler move in close proximity to the upper surface of the conveying reach. This insures that the cross-stream increment removed substantially represents the complete depth of the bulk material supported on the belt as well as the width of the increment defined between the opposed divider plates. Puncture or damage to the belt from lumps of bulk material is also substantially eliminated by modulating the belt in this manner.

While the features of the present invention as herein shown and described are especially adapted for taking cross-stream increment samples of bulk material from a moving conveyor belt, it is clear that the invention finds utility as well in obtaining such samples from stopped conveyor belts. However, the provision for obtaining samples from a moving belt makes it possible to continue the feed of bulk material to ultimate processing steps without interruption, offering significant advantages over sampling methods and apparatus previously employed. Specifically, the invention minimizes the need for surge capacity in the conveying line and reduces wear and tear on the machinery and associated components attendant repeated start and stop cycling thereof. Moreover, the invention eliminates the prior practice of conducting a side stream of the bulk material away from the main stream so that samples may be taken from the side stream during stoppage thereof. In this regard, it is to be appreciated that the sampling unit is capable of being incorporated into the main conveyor, thus eliminating the additional equipment previously required for conveying side streams of the bulk material for sampling purposes. The invention also eliminates interruption of the feed to important downstream processes dependent upon a continuous, uninterrupted supply of the bulk material while providing for taking of an ASTM Type I increment according to Condition B in a mechanized sampler for use with rapidly moving belts.

Although particular embodiments of the present invention have been described in the foregoing detailed description, it will be understood that the invention is capable of numerous rearrangements, modifications and substitutions of parts without departing from the scope of the invention as set forth in the claims below.

What is claimed:

1. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, and contour means for modulating the normal troughing of the belt to support and conform the cross-section of the belt to the arcuate path of said sampler means so that said sampler means moves in close proximity to the upper surface of the modulated belt and removes the cross-stream increment from the belt as the sampler means moves through its arcuate path across the belt, said contour means being support for movement from a retracted position in which said belt is substantially unmodulated to a supporting position in which said belt is modulated as aforesaid, and means for moving said contour means from said retracted position to said supporting position when said sampler means moves across said belt to accomplish removal of the cross stream increment.

2. The combination of claim 1, wherein said sampler means comprise a pair of spaced apart side plate members, frame means, a shaft on said frame means for supporting said plate members for rotary movement across said modulated belt, said side plate members having radially outward edges which are arcuate in outline and having leading edges formed on said side plate members and disposed to make initial contact with the bulk material on the belt as said sampler means moves across the belt, plate means interconnecting said side plate members extending from a position adjacent said arcuate edges towards said shaft, and motive means for imparting rotative forces to said shaft to rotate said sampler means through said arcuate path, whereby said side plate members segregate a cross-stream increment of the bulk material and together with said interconnecting plate means remove the cross-stream increment from the modulated belt.

3. The combination of claim 2, wherein the position of said interconnecting plate means adjacent said arcuate edges is spaced rearwardly from said leading edges of said side plate members relative to their direction of rotation.

4. The combination of claim 2, wherein means are provided for moving said sampler means between a lowered position in which said arcuate edges of said side plates are in close proximity to the upper surface of the modulated conveyor belt when said sampler means is rotated through said arcuate path across the modulated belt, and a raised position in which the arc circumscribed by the extremity of said arcuate edges of said side plates is located substantially above the upper surface of the bulk material supported on the belt, whereby said sampler means is substantially prevented from contacting bulk material on said belt when said sampler means is in the raised position and is rotated through said arcuate path.

5. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, contour means for modulating the normal troughing of the belt to support and conform the cross-section of the belt to the arcuate path of said sampler means so that said sampler means moves in close proximity to the upper surface of the modulated belt and removes the cross-stream increment from the belt as the sampler means moves through its arcuate path across the belt, said contour means being supported for movement from a retracted position in which said belt is substantially unmodulated to a supporting position in which said belt is modulated as aforesaid, and means for moving said contour means from said retracted position to said supporting position when said sampler means moves across said belt to accomplish removal of the cross stream increment, said sampler means comprising a pair of spaced apart side plate members, frame means, a shaft on said frame means for supporting said plate members for rotary movement across said modulated belt, said side plate members having radially outward edges which are arcuate in outline and having leading edges formed on said side plate members and disposed to make initial contact with the bulk material on the belt as said sampler means moves across the belt, plate means interconnecting said side plate members extending from a position adjacent said arcuate edges towards said shaft, and motive means for imparting rotative forces to said shaft to rotate said sampler means through said arcuate path, whereby said side plate members segregate a cross-stream increment of the bulk material and together with said interconnecting plate means remove the cross-stream increment from the modulated belt, and said motive means comprising a pair of cranks operatively connected to said shaft and first and second pneumatic cylinder means separately attached to each of said cranks and to said frame to impart rotational forces on said shaft through said cranks to accelerate and move said sampler means from a starting position through an arc across said modulated belt.

6. The combination of claim 5, wherein said first and second pneumatic cylinder means are supplied with pressurized air sequentially to accelerate said sampler means from a starting position through an arc across said modulated belt.

7. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, contour means for modulating the normal troughing of the belt to support and conform the cross-section of the belt to the arcuate path of said sampler means so that said sampler means moves in close proximity to the upper surface of the modulated belt and removes the cross-stream increment from the belt as the sampler means moves through its arcuate path across the belt, said contour means being supported for movement from a retracted position in which said belt is substantially unmodulated to a supporting position in which said belt is modulated as aforesaid, and means for moving said contour means from said retracted position to said supporting position when said sampler means moves across said belt to accomplish removal of the cross stream increment, said sampler means comprising a pair of spaced apart side plate members, frame means, a shaft on said frame means for supporting said plate members for rotary movement across said modulated belt, said side plate members having radially outward edges which are arcuate in outline and having leading edges formed on said side plate members and disposed to make initial contact with the bulk material on the belt as said sampler means moves across the belt, plate means interconnecting said side plate members extending from a position adjacent said arcuate edges towards said shaft, and motive means for imparting rotative forces to said shaft to rotate said sampler means through said arcuate path, whereby said side plate members segregate a cross-stream increment of the bulk material and together with said interconnecting plate means remove the cross-stream increment from the modulated belt, and said motive means including first and second overriding clutch means mounted on said shaft for separately transmitting rotative forces to said shaft to induce rotation of said sampler means, first pneumatic cylinder means actuable to engage said first overriding clutch means to impart a rotational force to said shaft through said first overriding clutch means to accelerate and move said sampler means from a starting position through a first arc, and second pneumatic cylinder means actuable to engage said second overriding clutch means to impart a rotational force to said shaft through said second overriding clutch means to further accelerate and move said sampler means from adjacent its position at the end of said first arc through a second arc.

8. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, contour means for modulating the normal troughing of the belt to support and conform the cross-section of the belt to the arcuate path of the sampler means so that said sampler means moves in close proximity to the upper surface of the modulated belt and removes the cross-stream increment from the belt as the sampler means moves through its arcuate path across the belt, said contour means being supported for movement from a retracted position in which said belt is substantially unmodulated to a supporting position in which said belt is modulated as aforesaid, means for moving said contour means from said retracted position to said supporting position when said sampler means moves across said belt to accomplish removal of the cross stream increment, and motive means for imparting rotational forces to said sampler means, said motive means comprising crank means connected to said sampler means for rotation therewith, first pneumatic cylinder means connected to said crank means at a first location on said crank means operable to impart rotational force on said sampler means through said crank means, and second pneumatic cylinder means connected to said crank means at a second location on said crank means and operable to impart rotational force on said sampler means through said crank means separately of said first cylinder means, said second location on said crank means being spaced circumferentially from said first location about the axis of rotation of said sampler means across the belt.

9. The combination of claim 8, wherein said first and second locations are spaced apart from about 40 to about 90 degrees on said crank means.

10. The combination of claim 8, wherein said first and second locations are spaced apart from about 60 to about 75 degrees on said crank means.

11. The combination of claim 8, wherein said first and second cylinder means each comprise first and second double acting pneumatic cylinders, each having a piston rod with one end extending out of the cylinder and being movably supported therein for being advanced out of and retracted into the cylinder, a first port located on the cylinder for admitting compressed air into the cylinder to cause advancement of the rod and for exhausting air out of the cylinder when said rod is retracted, a second port located on the cylinder for admitting compressed air into the cylinder to cause retraction of the rod and for exhausting air out of the cylinder when the rod is advanced, said rod being connected at its end extending out of the cylinder to the respective first or second location, and means for selectively and sequentially applying compressed air to said first and second ports of each of said cylinders so that said cylinders hold said sampler means in the ready position and coact to impart rotational forces on said sampler means at selected sampling intervals to cause said sampler means to rotate across the belt and remove the cross-stream sample increment therefrom.

12. The combination of claim 11, wherein said first and second pneumatic cylinders are configured and disposed relative to one another and to said sampler means so that when said sampler means is in its ready position, said first and second locations are both off center relative to the axis of rotation of said sampler means and said first location is spaced from said second location towards the direction in which said sampler means is to be rotated.

13. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, contour means for modulating the normal troughing of the belt to support and conform the cross-section of the belt to the arcuate path of said sampler means so that said sample means moves in close proximity to the upper surface of the modulated belt and removes the cross-stream increment from the belt as the sampler means moves through its arcuate path across the belt, said contour means being support for movement from a retracted position in which said belt is substantially unmodulated to a supporting position in which said belt is modulated as aforesaid, and means for moving said contour means from said retracted position to said supporting position when said sampler means moves across said belt to accomplish removal of the cross stream increment, and said sample means comprising a sample sweep mounted for rotation about a rotative axis with a pair of cranks on the rotative axis attached to the sweep, the cranks being angularly displaced from one another and having a double acting pneumatic cylinder operatively connected to each crank, valve means for alternately pressurizing and venting chambers of each double acting pneumatic cylinder, said sweep being adapted to pass through the bulk material on said belt as said sweep is rotated about said rotative axis to remove the cross-stream increment from the modulated belt, and sequencing means for controlling and rotating the sweep comprising means for pressurizing a selected chamber of each cylinder to provide balancing forces to hold said sweep in a predetermined ready position, thereafter alternately pressurizing and venting selected chambers of said cylinders to provide forces to rotate said sweep through a 360° arc which passes through the bulk material on said belt, and thereafter pressurizing selected chambers of said cylinders to return said sweep to the ready position.

14. A combination comprising a belt conveyor having a conveyor belt for conveying bulk material disposed thereon and drive means for driving the belt, the belt being supported for longitudinal movement in a trough-like configuration on rolling support means such that the belt has an angular, substantially non-arcuate cross-section, sampler means movable through an arcuate path across the belt for removing a cross-section increment of bulk material therefrom, contour means for modulating the normal troughing of the belt to support and conform the cross-section of the belt to the arcuate path of said sampler means so that said sampler means moves in close proximity to the upper surface of the modulated belt and removes the cross-stream increment from the belt as the sampler means moves through its arcuate path across the belt, said contour means being supported for movement from a retracted position in which said belt is substantially unmodulated to a supporting position in which said belt is modulated as aforesaid, and means for moving said contour means from said retracted position to said supporting position when said sampler means moves across said belt to accomplish removal of the cross stream increment, said sample means including a sample sweep mounted for rotation about a rotative axis with a pair of cranks on the rotative axis attached to the sweep, the cranks being angularly displaced from one another and having a double acting pneumatic cylinder operatively connected to each crank, valve means for alternately pressurizing and venting chambers of each double acting pneumatic cylinder, said sweep being adapted to pass through the bulk material on said belt as said sweep is rotated about said rotative axis to remove the cross-section increment from the modulated belt, and sequencing means for controlling and rotating the sweep comprising means for pressurizing a selected chamber of each cylinder to provide balancing forces to hold said sweep in a predetermined ready position, thereafter alternately pressurizing and venting selected chambers of said cylinders to provide forces to rotate said sweep through a 360° arc which passes through the bulk material on said belt, after said sweep has passed through the body of material, pressurizing a selected chamber in one of said cylinders momentarily to oppose the force of the chamber in the other cylinder to decelerate said sweep and eject material from said sweep, and thereafter pressurizing selected chambers in said cylinders to return said sweep to the ready position.

* * * * *

UNITED STATES PATENT AND TRADEMARK OFFICE
CERTIFICATE OF CORRECTION

PATENT NO. : 4,884,462
DATED : December 5, 1989
INVENTOR(S) : John B. Long

It is certified that error appears in the above-identified patent and that said Letters Patent is hereby corrected as shown below:

Column 14, line 7, delete "sample" and insert -- sampler --.

Column 14, line 12, delete "support" and insert -- supported --.

Signed and Sealed this

Twenty-seventh Day of November, 1990

Attest:

HARRY F. MANBECK, JR.

*Attesting Officer*          *Commissioner of Patents and Trademarks*